United States Patent [19]
Prashad et al.

[11] Patent Number: 6,100,401
[45] Date of Patent: Aug. 8, 2000

[54] PROCESS FOR PREPARING THE D-THREO ISOMER OF METHYLPHENIDATE HYDROCHLORIDE

[75] Inventors: Mahavir Prashad, Montville; Denis Har, Harrison, both of N.J.

[73] Assignee: Novartris AG, Basel, Switzerland

[21] Appl. No.: 09/063,100

[22] Filed: Apr. 20, 1998

[51] Int. Cl.$^7$ .................................................. C07D 211/34
[52] U.S. Cl. .......................................................... 546/233
[58] Field of Search ............................................. 546/233

[56] References Cited

U.S. PATENT DOCUMENTS

| | | | |
|---|---|---|---|
| 2,957,880 | 10/1960 | Rometsch | 546/233 |
| 5,407,938 | 4/1995 | Fisher et al. | 514/278 |
| 5,504,253 | 4/1996 | Van Wagenen et al. | 564/374 |
| 5,733,756 | 3/1998 | Zeitlin et al. | 435/122 |

FOREIGN PATENT DOCUMENTS

| | | |
|---|---|---|
| 7247286 | 9/1995 | Japan . |
| WO 97/27176 | 7/1997 | WIPO . |
| WO 97/28124 | 8/1997 | WIPO . |
| WO 97/32851 | 9/1997 | WIPO . |
| WO 97/35836 | 10/1997 | WIPO . |
| 98/25902 | 6/1998 | WIPO . |

OTHER PUBLICATIONS

Kajima et al. "Optical resolution by high performance liquid chromatography . . ." AA Accession No. 52–10–E–00052, 1989.

Duncan et al. "normal phase TLC separation of enantiomers using chiral . . ." AA Accession No. 53–06–G–00004, 1990.

Lim H.K. et al., Journal of Chromatography vol. 328, pp. 378–386 (1985).

Journ. of Pharmacol. & Experimental Therapeutics, Patrick et al., vol. 241, pp. 152–158 (1997).

Clin.Pharmacol. & Therapeutics, Srinivas et al., vol. 52, No. 5, pp. 561–568 (1992).

Journ. of Chromatagraphy, vol. 494, pp. 420–423 (1989).

J. Med. Chem., Thai, et al., vol. 41, pp. 591–601 (1998).

*Primary Examiner*—Ceila Chang
*Attorney, Agent, or Firm*—Joseph J. Borovian

[57] ABSTRACT

A process for preparing the d-threo isomer of methylphenidate hydrochloride comprising resolving the racemic mixture of threo methylphenidate hydrochloride with dibenzoyl-D-tartaric acid to obtain a dibenzoyl-D-tartrate salt enriched with the d-threo isomer of methylphenidate in a first step, basifying the tartrate salt to obtain the free base form of the d-threo isomer of methylphenidate in a second step, converting the free base to the hydrochloride salt form of the d-threo isomer of methylphenidate in high optical purity in a third step, and recrystallizing the hydrochloride salt form to obtain the desired d-threo isomer in a higher optical purity.

16 Claims, No Drawings

PROCESS FOR PREPARING THE D-THREO ISOMER OF METHYLPHENIDATE HYDROCHLORIDE

FIELD OF THE INVENTION

The present invention relates to the area of resolution processes and, more particularly, relates to an improved process for preparing the d-threo isomer of methylphenidate hydrochloride employing dibenzoyl-D-tartaric acid as the resolving agent.

BACKGROUND OF THE INVENTION

Methylphenidate was first prepared as a mixture of the erythro and threo racemates. Subsequent studies of the two racemic mixtures revealed that the therapeutic activity resides in the threo diastereomer.

Racemic threo methylphenidate hydrochloride is a mild nervous system stimulant which is marketed for the treatment of children with Attention Deficit Hyperactivity Disorder (ADHD). Further studies of the threo diastereomer revealed that the preferred therapeutic activity resides in the d-threo (or 2R,2'R enantiomer. More particularly, it has been found that the d-threo enantiomer is between five and thirty-eight times more active then the corresponding l-threo enantiomer. In addition, it has been shown that there are significant metabilic differences between the two enantiomers.

To date, there have been a few methods disclosed in the literature for preparing the d-threo enantiomer of methylphenidate hydrochloride. U.S. Pat. No. 2,957,880 discloses a rather tedious sequence involving the resolution of the amide derivative of the corresponding erythro isomer, conversion to the threo isomer, followed by the hydrolysis of the amide to the corresponding acid, and esterification of the resulting acid with methanol. In the Journal of Pharmacology and Experimental Therapeutics, Vol. 241, pgs. 152–158 (1987), the d-threo enantiomer is prepared by resolving the racemic mixture of threo methylphenidate employing (R)-(−)-1,1'-binaphthyl-2,2'-diyl hydrogen phosphate. In WO 97/27176, the d-threo enantiomer is prepared by resolving racemic threo methylphenidate employing a di-aroyltartaric acid, preferably a di-toluoyltartaric acid, whereas in WO 97/32851, the d-threo enantiomer is prepared by resolving racemic threo methylphenidate employing (−)-menthoxyacetic acid. Although the latter three processes are believed to be more efficient than the resolution method disclosed in U.S. Pat. No. 2,957,880, they all exhibit drawbacks which make them unattractive from a commercial standpoint. To wit, the use of (R)-(−)-1,1'-binaphthyl-2,2'-diyl hydrogen phosphate as the resolving agent in the commercial Pharmacology and Experimental Therapeutics article and the need for further recrystallizations to attain the desired purity renders the cost of the commercial process employing this method to be prohibitive. As to the latter two methods, they both involve the isolation of the free base form of the racemic mixture of threo methylphenidate prior to resolution. Accordingly, a need exists for a more practical and economic process for preparing the d-threo isomer of methylphenidate hydrochloride.

SUMMARY OF THE INVENTION

The present invention relates to an improved process for preparing the d-threo isomer of methylphenidate hydrochloride employing di-benzoyl-D-tartaric acid as the resolving agent. The process of the present invention is believed to be more practical and economical since it avoids the isolation of, or conversion to, the free base form of the racemic mixture of threo methylphenidate prior to resolution, i.e., it utilizes the hydrochloride salt form of the racemic mixture of threo-methylphenidate directly. More particularly, the process of the instant invention involves the resolution of d,l-threo methylphenidate hydrochloride with dibenzoyl-D-tartaric acid to yield the desired tartrate salt enriched with the d-threo (2R,2'R) isomer of methylphenidate in a first step, the basification of said salt to obtain the free base form of the desired d-threo isomer in a second step, the conversion of the free base into the hydrochloride salt form of the desired d-threo isomer in high optical purity in a third step, and the recrystallization of said salt to obtain the desired d-threo isomer in a higher optical purity.

DETAILED DESCRIPTION OF THE INVENTION

The present invention relates to an improved process for preparing the d-threo isomer of methylphenidate hydrochloride directly from the racemic mixture of threo methylphenidate hydrochloride by a four-step process as depicted below:

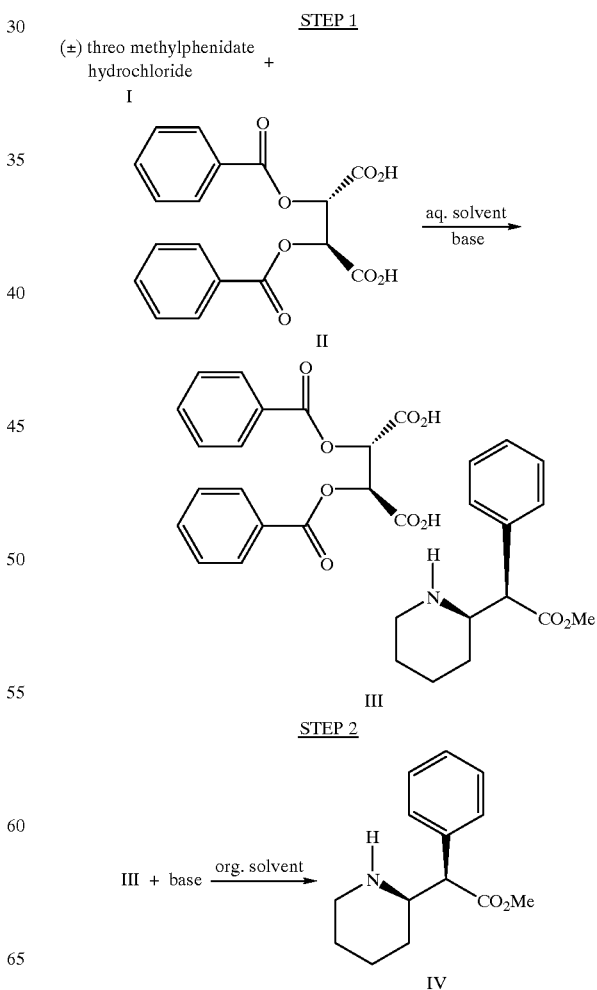

-continued

STEP 3

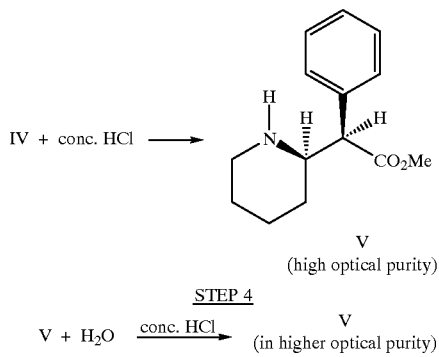

V
(high optical purity)

STEP 4

V + H₂O $\xrightarrow{\text{conc. HCl}}$ V (in higher optical purity)

With respect to the individual steps, Step 1 involves the reaction of the racemic mixture of threo methylphenidate hydrochloride with at least a nearly equimolar amount of di-benzoyl-D-tartaric acid in the presence of an aqueous solvent, e.g., a mixture of a lower alkanol and water, and a base to obtain the desired tartrate salt of formula III. The aqueous solvent is preferably a mixture of methanol or ethanol in water in a ratio of between 1.7 and 2.1:1, more preferably a mixture of methanol and water in a ratio of about 2:1. Any base may be employed in the reaction as long as the salt of the base with the resolving agent, viz., the di-benzoyl-D-tartaric acid, remains dissolved in the aqueous solvent. Suitable bases that may be employed are 4-methylmorpholine, an alkali metal hydroxide or a tri-lower alkyl amine, preferably 4-methylmorpholine, sodium hydroxide or triethylamine, more preferably 4-methylmorpholine. The reaction is conducted at an initial temperature of from 40° to 50° C. for a period of between 30 and 90 minutes, then at a temperature of from 15° to 30° C. for a period of between 45 minutes and 2 hours, and finally at a temperature of from 0° to 10° C. for a period of between 90 minutes and 3 hours.

The second step involves the basification of the tartrate salt obtained in Step 1, i.e. the compound of formula III, with an alkali metal hydroxide solution, preferably a sodium hydroxide solution, in the presence of an inert, organic solvent, preferably isopropyl acetate, to obtain the free base form of the desired d-threo isomer, i.e., the compound of formula IV. The basification is carried out at a temperature of from 15° to 30° C. for a period of between 30 and 60 minutes.

The third step concerns the conversion of the free base obtained in Step 2, i.e, the compound of formula IV, into the hydrochloride salt form of the desired d-threo isomer in high optical purity. The conversion is carried out by adding concentrated hydrochloric acid to the free base (which has been pre-cooled to between 0° and 5° C.), and then allowing the mixture to react at a temperature of from 5° to 25° C. for a period of between 30 minutes and 2 hours to obtain the compound of formula V.

The last step involves the recrystallization of the hydrochloride salt obtained in Step 3, i.e., the compound of formula V, by the addition of concentrated hydrochloric acid to an aqueous solution of the hydrochloride salt. The resultant mixture is then allowed to react at a temperature of from 0° to 10° C. for a period of between 30 and 60 minutes to obtain the hydrochloride salt in a higher optical purity.

Although not essential, it is preferred that the resolution in Step 1 be carried out in the presence of a crystallization-inducing amount of pure dibenzoyl-D-tartrate salt seeds enriched with the d-threo isomer of methylphenidate, which seeds may be obtained by adding a solution of the free base form of the desired d-threo isomer of methylphenidate in ethyl acetate to an equimolar solution of dibenzoyl-D-tartaric acid in ethyl acetate. The mixture is then allowed to react at a temperature of from 0° to 10° C. for a period of between 30 and 60 minutes.

Alternatively, the resolution in Step 1 may be carried out by reacting the racemic mixture of threo methylphenidate hydrochloride with an equimolar amount of the pre-formed salt of 4-methylmorpholine and dibenzoyl-D-tartaric acid essentially as described above, preferably in the presence of pure dibenzoyl-D-tartrate salt seeds enriched with the d-threo isomer of methylphenidate, to obtain the desired tartrate salt of formula III. The pre-formed salt may be obtained by reacting dibenzoyl-D-tartaric acid with an equimolar amount of 4-methylmorpholine in the presence of an inert, organic solvent, preferably isopropyl acetate, at a temperature of from 15° to 25° C. for a period of between 10 and 30 minutes.

As alluded to above, racemic threo methylphenidate hydrochloride is known and commercially available, as is the resolving agent employed in Step 1, i.e., the dibenzoyl-D-tartaric acid. In the latter connection, another advantage of the process of this invention is that the resolving agent is recyclable. Thus, the dibenzoyl-D-tartaric acid may be recovered by combining the filtrate from Step 1 with the aqueous layer from Step 2, basifying the combined mixture and extracting with isopropyl acetate, treating the resultant aqueous layer with concentrated hydrochloric acid and extracting with isopropyl acetate, filtering and treating the resultant residue with isopropyl alcohol and then with heptane. The recovered dibenzoyl-D-tartaric acid is of comparable purity to that of the commercially available material. A resolution of racemic threo methylphenidate hydrochloride with the recovered material yielded the desired tartrate salt enriched with the d-threo isomer of methylphenidate.

As is fairly evident, the l-threo (or 2S,2'S) isomer of methylphenidate hydrochloride in high purity may be prepared by the process of this invention by utilizing dibenzoyl-L-tartaric acid as the resolving agent in Step 1.

Although the desired tartrate salt obtained in Step 1 described above may, if desired, be purified by conventional techniques such as recrystallization, the crude tartrate salt is advantageously employed in Step 2 described above without purification.

The following examples are for purposes of illustration only and are not intended to limit in any way the scope of the instant invention

EXAMPLE 1

Preparation of d-threo isomer of methylphenidate hydrochloride (in the presence of pure dibenzoyl-D-tartrate salt seeds)

a) preparation of dibenzoyl-D-tartrate salt enriched with the d-threo isomer of methylphenidate To a 3-L, 4-necked, round-bottomed flask, equipped with a mechanical stirrer, digital thermometer, nitrogen inlet-outlet, heating-cooling bath and addition funnel, is added 129.5 g (0.48 mol) of d,l-threo methylphenidate hydrochloride and 172.0 g (0.48 mol) of dibenzoyl-D-tartaric acid. To the resultant mixture is added 624 ml of methanol and the suspension is stirred under nitrogen at a temperature of from 20° to 25° C., after which time 48.55 g of 4-methylmorpholine (0.48 mol) is added, over a period of 5 to 10 minutes, while the temperature is maintained between 29° and 31° C. The resultant clear solution is then heated to between 40° and 45° C., over a period of 15 minutes, after which time 312 ml of deionized plant water is added, over a period of 5 to 10 minutes, while the temperature is maintained between 40° and 45° C. To the resultant clear solution is then added 60 mg of pure dibenzoyl-D-tartrate salt seeds enriched with the d-threo isomer of methylphenidate (obtained essentially as described earlier in the specification), and the mixture is then cooled to a temperature between 20° and 25° C., over a period of 1 hour, and then maintained at this temperature for another hour with stirring. The mixture is then cooled to a temperature between 0° and 5° C. over a period of 15 minutes and then maintained at this temperature for another 2 hours with stirring. The mixture is then filtered and the residue is washed with 210 ml of a pre-cooled (0° to 5° C.) mixture of methanol and water (in a 2:1 v/v ratio) in 3 equal portions of 70 ml each and then dried at a temperature between 50° and 55° C. (100 mmHg) to obtain the desired tartrate salt as a white solid (2R,2'R:2S,2'S ratio is 99.36:0.64).

b) preparation of the free base form of d-threo methylphenidate

To a 2-L, 4-necked, round-bottomed flask, equipped with a mechanical stirrer, digital thermometer, nitrogen inlet-outlet and addition funnel, is added 125.3 g of the tartrate salt obtained in a) above and 400 ml of isopropyl acetate and the mixture is stirred at a temperature between 20° and 25° C. under nitrogen. To the mixture is then added a pre-cooled (~20° C.) solution of 21.18 g of sodium hydroxide in 400 ml of water, over a period of 15 minutes, while the temperature is maintained between 20° and 25° C. The resultant suspension is then stirred until all of the solid dissolves (~10–15 minutes), after which time the layers are separated. The aqueous layer is then extracted with 200 ml of isopropyl acetate. The combined organic layers are then washed with 30 ml of water and then line-filtered to obtain a solution of the desired free base.

c) preparation of the hydrochloride salt form of d-threo-methylphenidate in a high optical purity To a 2-L, 4-necked round-bottomed flask, equipped with a mechanical stirrer, digital thermometer, nitrogen inlet-outlet, cooling bath and addition funnel, is added ~675 ml of the solution of free base obtained in b) above which is then cooled to a temperature between 0° and 2° C. To the cooled solution is then added, over a period of 10 minutes, 34.9 g of concentrated hydrochloric acid (31%), while the temperature is maintained at less than 10° C. The reaction mixture is then warmed to a temperature between 20° and 22° C., over a period of 45 minutes, filtered and the resultant solid is washed with 100 ml of isopropyl acetate, in 2 equal portions of 50 ml each, and dried at a temperature between 55° and 58° C. (100 mmHg) to obtain the desired hydrochloride salt as a white solid (2R,2'R:2S,2'S ratio is 99.68:0.32).

d) preparation of the title compound in a higher optical purity

To a 500 ml, 4-necked, round-bottomed flask, equipped with a mechanical stirrer, digital thermometer, nitrogen inlet-outlet, heating mantle, condenser and addition funnel, is added 64 g of deionized water which is then heated to a temperature of between 74° and 75° C. To the heated water is then added 55.0 g of the hydrochloride salt obtained in c) above, and the mixture is heated to a temperature between 80° and 82° C. The resultant clear solution is then cooled to a temperature of between 20° and 22° C., over a period of 45 minutes. To the resultant heterogeneous mixture is then added 24 g of concentrated hydrochloric acid (31%), over a period of 10 minutes, while the temperature is maintained at less than 25° C. The mixture is then cooled to a temperature between 0° and 5° C., over a period of 15 minutes, and then stirred at this temperature for an additional 30 minutes. The mixture is then filtered and the resultant solid is washed with 15 ml of pre-cooled water (between 0° and 5° C.) in 2 equal portions of 7.5 ml each, and dried at a temperature between 50° and 55° C. (100 mmHg) to obtain the desired title compound as a white powder (2R,2'R:2S,2'S ratio is 100:0, i.e., the 2S,2'S enantiomer was undetectable).

EXAMPLE 2

Preparation of d-threo isomer of methylphenidate hydrochloride (in the absence of pure dibenzoyl-D-tartrate salt seeds)

a) preparation of dibenzoyl-D-tartrate salt enriched with the d-threo isomer of methylphenidate Following essentially procedure a) of Example 1, with the exception that the pure dibenzoyl-D-tartrate salt seeds are not added, the desired tartrate salt is obtained as a white solid.

b) preparation of the title compound

Following essentially procedures b), c) and d) of Example 1, with the exception that an approximately equivalent amount of the tartrate salt obtained in a) above is used as the starting material in procedure b) instead of the tartrate salt obtained in procedure a) of Example 1, the title compound is obtained in an enantiomer ratio equivalent to that of Example 1.

EXAMPLE 3

Preparation of l-threo isomer of methylphenidate hydrochloride a) preparation of dibenzoyl-L-tartrate salt enriched with the l-threo isomer of methylphenidate Following essentially procedure a) of Example 1, with the exception that an approximately equivalent amount of dibenzoyl-L-tartaric acid is used instead of dibenzyl-D-tartaric acid, and with the further exception that the pure dibenzoyl-D-tartrate salts are not added, the desired tartrate salt is obtained as a white solid.

b) preparation of the title compound

Following essentially procedures b), c) and d) of Example 1, with the exception that an approximately equivalent amount of the tartrate salt obtained in a) above is used as the starting material in procedure b) instead of the tartrate salt obtained in procedure a) of Example 1, the title compound is obtained in an enantiomer ratio equivalent to that of Example 1.

EXAMPLE 4

Procedure for the recovery of the dibenzoyl-D-tartaric acid resolving agent a) separation of resolving agent and free base form of d-threo isomer of methylphenidate To a 5-L, 4-necked, round-bottomed flask, equipped with a mechanical stirrer, digital thermometer, nitrogen inlet-outlet and addition funnel, is added ~1.3L of the filtrate from procedure a) in Example 1 and ~400 ml of the aqueous layer from procedure b) in Example 1. To this mixture is added a pre-cooled (~20° C.) solution of 42 g of sodium hydroxide in 200 ml of deionized water, over a period of 20 minutes, while the temperature is maintained at less than 25° C. To the resultant mixture is added 700 ml of isopropyl acetate and this mixture is then stirred at a temperature between 22° and 25° C. for 5 minutes. The layers are then separated and the aqueous layer is extracted with 350 ml of isopropyl acetate and saved.

b) recovery of resolving agent

To a 5-L, 4-necked, round-bottomed flask, equipped with a mechanical stirrer, digital thermometer, nitrogen inlet-outlet, cooling bath and addition funnel, containing 1.7L of the aqueous layer obtained in a) above is added 150 ml of concentrated hydrochloric acid (31%), over a period of 20 minutes, while the temperature is maintained at between 20° and 22° C. To this mixture is added 700 ml of isopropyl acetate and the resultant mixture is stirred for 10 minutes while the temperature is maintained between 20° and 22° C. The layers are separated and the aqueous layer is extracted with 350 ml of isopropyl acetate. The combined organic layers are then washed with 100 ml of deionized water, line-filtered and concentrated. To the resultant residue is added 175 ml of isopropyl alcohol and the mixture is heated to a temperature between 70° and 75° C. To the resultant solution is added 175 ml of heptane while the temperature is maintained between 70° and 75° C. The solution is then cooled to a temperature of between 22° and 25° C. with stirring over a period of 1 hour, and stirred at this temperature for an additional 1 hour. The mixture is then cooled to a temperature of between 0° and 5° C. and stirred at this temperature for 1 hour. The mixture is then filtered and the residue is washed with 100 ml of a pre-cooled (0° to 5° C.) mixture of isopropyl alcohol and heptane (in a 1:1 v/v ratio) in 2 equal portions of 50 ml each. The residue is then dried at a temperature between 70° and 72° C. (100 mmHg) to obtain the desired resolving agent as a white powder in a purity equivalent to the commercial material.

EXAMPLE 5

Procedure for preparing the pre-formed salt of 4-methylmorpholine and dibenzoyl-D-tartaric acid To a 500 ml, 4-necked, round-bottomed flask, equipped with a mechanical stirrer, digital thermometer, cooling bath and addition funnel, containing a solution of 35.8 g (0.10 mol) of dibenzoyl-D-tartaric acid in 100 ml of isopropyl acetate is added, dropwise over a period of 15 minutes, 11.0 g (0.108 mol) of 4-methylmorpholine, while the temperature is maintained at less than 25° C. The mixture is then filtered and the crude residue is washed with 9 ml of isopropyl acetate in 3 equal portions of 3 ml each. The resultant residue is then dried at a temperature between 50° and 55° C. (100 mmHg) to obtain the desired salt.

EXAMPLE 6

Preparation of d-threo isomer of methylphenidate hydrochloride (employing the pre-formed salt of 4-methylmorpholine and dibenzoyl-D-tartaric acid).

a) preparation of dibenzoyl-D-tartrate salt enriched with the d-threo isomer of methylphenidate To a 500 ml, 4-necked, round-bottomed flask, equipped with a mechanical stirrer, digital thermometer, nitrogen inlet-outlet, heating-cooling bath and addition funnel, is added 12.95 g (48 mmol) of d-l-threo methylphenidate hydrochloride and 22.05 g (48 mmol) of the salt of Example 5. To the resultant mixture is added 62 ml of methanol and the suspension is heated to a temperature between 45° and 50° C. To the resultant clear solution is then added 31 ml of water and ~5 mg of pure dibenzoyl-D-tartrate salt seeds enriched with the d-threo isomer of methylphenidate (obtained essentially as described earlier in the specification, and the mixture is then cooled to a temperature between 20° and 25° C., over a period of 1 hour, and then maintained at this temperature for another hour with stirring. The mixture is then cooled to a temperature between 0° and 5° C. over a period of 15 minutes and then maintained at this temperature for another 2 hours with stirring. The mixture is then filtered and the residue is washed with 21 ml of a pre-cooled (0° to 5° C.) mixture of methanol and water (in a 2:1 v/v ratio) in 3 equal portions of 7 ml each and then dried at a temperature between 50° and 55° C. (100 mmHg) to obtain the desired tartrate salt as a white solid.

b) preparation of the title compound

Following essentially procedures b), c) and d) of Example 1, with the exception that an approximately equivalent amount of the tartrate salt obtained in a) above is used as the starting material in procedure b) instead of the tartrate salt obtained in procedure a) of Example 1, the title compound is obtained in an enantiomer ratio equivalent to that of Example 1.

What is claimed is:

1. A process for preparing the d-threo isomer of methylphenidate hydrochloride directly from the racemic mixture of threo methylphenidate hydrochloride comprising the steps of:
   1) resolving d,l-threo methylphenidate hydrochloride with a preformed salt of 4-methylmorpholine and dibenzoyl-D-tartaric acid in the presence of a crystallization-inducing amount of pure dibenzoyl-D-tartrate salt seeds enriched with the d-threo isomer of methylphenidate to obtain a dibenzoyl-D-tartrate salt enriched with the d-threo isomer of methylphenidate;
   2) basifying the tartrate salt prepared in Step 1 to obtain the free base form of d-threo methylphenidate;
   3) converting the free base prepared in Step 2 into the hydrochloride salt form of d-threo methylphenidate in high optical purity; and
   4) recrystallizing the salt prepared in Step 3 to obtain the desired d-threo isomer in a higher optical purity.

2. A process according to claim 1 wherein the first step is carried out at an initial temperature of from 40° to 50° C. for a period of between 30 and 90 minutes, then at a temperature of from 15° to 30° C. for a period of between 45 minutes and 2 hours and finally at a temperature of from 0° to 10° C. for a period of between 90 minutes and 3 hours.

3. A process according to claim 1 wherein the second step is carried out with an alkali metal hydroxide solution.

4. A process according to claim 3 wherein the second step is carried out with a sodium hydroxide solution.

5. A process according to claim 1 wherein the second step is carried out in the presence of an inert, organic solvent.

6. A process according to claim 5 wherein the solvent is isopropyl acetate.

7. A process according to claim 1 wherein the second step is carried out at a temperature of from 15° to 30° C. for a period of between 30 and 60 minutes.

8. A process according to claim 1 wherein the third step is carried out by adding concentrated hydrochloric acid to the free base obtained in the second step which is pre-cooled to a temperature between 0° and 5° C.

9. A process according to claim 8 wherein the third step is carried out at a temperature of from 5° to 30° C. for a period of between 30 minutes and 2 hours.

10. A process according to claim 1 wherein the fourth step is carried out by adding concentrated hydrochloric acid to an aqueous solution of the hydrochloride salt obtained in the third step.

11. A process according to claim 10 wherein the fourth step is carried out at a temperature of from 0° to 10° C. for a period of between 30 and 60 minutes.

12. A process according to claim 1 wherein the pre-formed salt in the first step is present in an equimolar amount.

13. A process according to claim 1 wherein the first step is carried out in the presence of an aqueous solvent.

14. A process according to claim 13 wherein the aqueous solvent is a mixture of a lower alkanol and water.

15. A process according to claim 14 wherein the aqueous solvent is a mixture of methanol or ethanol and water in a ratio of between 1.7 and 2.1:1.

16. A process according to claim 15 wherein the aqueous solvent is a mixture of methanol and water in a ratio of about 2:1.

* * * * *

UNITED STATES PATENT AND TRADEMARK OFFICE
CERTIFICATE OF CORRECTION

PATENT NO. : 6,100,401
DATED : August 8, 2000
INVENTOR(S) : PRASHAD ET AL.

It is certified that error appears in the above-indentified patent and that said Letters Patent is hereby corrected as shown below:

Column 8, claim 1, line 1; "d-threo" should read -- d-threo --

Column 8, claim 1, line 5; "d,1-threo" should read -- d,1-threo --

Column 8, claim 1, lines 11, 13, 15 and 18; "d-threo" should read -- d-threo --

Signed and Sealed this

Seventeenth Day of April, 2001

*Attest:*

NICHOLAS P. GODICI

*Attesting Officer*   Acting Director of the United States Patent and Trademark Office